US005843051A

United States Patent [19]

Adams et al.

[11] Patent Number: 5,843,051
[45] Date of Patent: Dec. 1, 1998

[54] INTRAVASCULAR DEVICE FOR CORONARY HEART TREATMENT

[75] Inventors: Daniel O. Adams, Orono; Scott P. Thome, Waite Park, both of Minn.

[73] Assignee: SciMed Life Systems, Inc., Maple Grove, Minn.

[21] Appl. No.: 602,920

[22] Filed: Mar. 21, 1996

Related U.S. Application Data

[62] Division of Ser. No. 303,590, Sep. 9, 1994, Pat. No. 5,527,292, which is a continuation of Ser. No. 874,079, Apr. 24, 1992, abandoned, which is a continuation-in-part of Ser. No. 605,398, Oct. 29, 1990, abandoned.

[51] Int. Cl.$^6$ .................................................. A61M 5/00
[52] U.S. Cl. ........................ 604/280; 604/283; 604/164; 604/264; 604/171
[58] Field of Search ............................... 604/93, 158, 160, 604/166, 164, 171, 264, 280, 283

[56] References Cited

U.S. PATENT DOCUMENTS

| | | | |
|---|---|---|---|
| 2,657,691 | 11/1953 | Nordstrom, Jr. | 606/108 |
| 3,262,449 | 7/1966 | Pannier . | |
| 3,297,030 | 1/1967 | Czorny et al. | 128/214.2 |
| 3,550,591 | 12/1970 | MacGregor | 128/214.2 |
| 3,559,643 | 2/1971 | Pannier et al. | 128/214.4 |
| 3,682,173 | 8/1972 | Center | 128/214.4 |
| 3,777,743 | 12/1973 | Binard et al. | 606/119 |
| 3,877,429 | 4/1975 | Rasmuoff | 604/158 |
| 4,000,743 | 1/1977 | Weaver | 606/119 |
| 4,187,848 | 2/1980 | Taylor | 128/247 |
| 4,198,981 | 4/1980 | Sinnreich | 606/119 |
| 4,345,596 | 8/1982 | Young | 128/214 |
| 4,354,491 | 10/1982 | Marbry | 604/161 |
| 4,369,790 | 1/1983 | McCarthy | 604/280 |

(List continued on next page.)

FOREIGN PATENT DOCUMENTS

| | | | |
|---|---|---|---|
| 0 628 292 | 10/1961 | Canada | 604/160 |
| 0 397 357 | of 0000 | European Pat. Off. . | |
| 0 002 607 | 6/1979 | European Pat. Off. . | |
| 0 231 601 | 8/1987 | European Pat. Off. . | |
| 0 277 366 | 8/1988 | European Pat. Off. . | |
| 0 282 143 | 9/1988 | European Pat. Off. . | |
| 0 627 828 | 8/1978 | U.S.S.R. . | |

OTHER PUBLICATIONS

Schneider, Inc., Product Brochure for Monorail® GEX™, Copyright Oct. 1990.
USCI, Product Brochure for Probing Catheter.
Cordis Corp., Product Brochure for The Cordis Shuttle™ Catheter (2 pages), Copyright Dec. 1990.
A Technique For Exchanging A Clotted Intravascular Catheter Using the Original Arteriopuncture Site—M. Leon Skolnick, M.D., Syracuse, New York.
"Replacing the Occluded Percutaneous Nephrostomy Catheter", *Radiology*, p. 824, Dec. 1981, Baron et al.
"Spiral Exchange Cannula for the Occluded Drainage Catheter", *Radiology*, pp. 543–544, Nov. 1985, McCain et al.
"An Alternate Method for Repair of a Leaking Arterial Chemotherapy Infusion Catheter", *Journal of Surgical Oncology*, pp. 27–28, 1987, Burkhalter et al.

*Primary Examiner*—Richard J. Apley
*Assistant Examiner*—Benjamin K. Koo
*Attorney, Agent, or Firm*—Kinney & Lange, P.A.

[57] ABSTRACT

An intravascular device having an elongated flexible tube sized for insertion into a coronary vessel beyond a distal end of a guide catheter. In use, the flexible tube has its proximal end within a guide catheter and has its distal end extending to a treatment site in a coronary artery. The device also including a push rod attached to a proximal end of the flexible tube to facilitate placement of the flexible tube within the coronary artery requiring treatment. In certain applications, the intravascular device is used as a drug (or other fluid) delivery device or as an aspiration device. In other applications, the intravascular device is used as a guiding means for placement of an angioplasty device, such as a guide wire or a balloon catheter. Additionally, an attachment tube may be provided which is designed to couple with a proximal end of the flexible tube to provide a continuous conduit for aspiration or fluid delivery to a treatment site in a coronary artery.

9 Claims, 10 Drawing Sheets

U.S. PATENT DOCUMENTS

| | | | |
|---|---|---|---|
| 4,412,932 | 11/1983 | Kling et al. | 604/164 |
| 4,449,532 | 5/1984 | Storz | 128/341 |
| 4,534,363 | 8/1985 | Gold | 128/772 |
| 4,581,017 | 4/1986 | Sahota | 604/101 |
| 4,581,019 | 4/1986 | Curelaru et al. | 604/280 |
| 4,581,025 | 4/1986 | Timmermans | 604/264 |
| 4,616,652 | 10/1986 | Simpson | 128/344 |
| 4,619,644 | 10/1986 | Scott | 604/53 |
| 4,631,059 | 12/1986 | Wolvek et al. | 604/280 |
| 4,687,469 | 8/1987 | Osypka | 604/280 |
| 4,696,667 | 9/1987 | Masch | 604/53 |
| 4,723,948 | 2/1988 | Clark et al. | 604/283 |
| 4,726,369 | 2/1988 | Mar | 128/303 |
| 4,747,833 | 5/1988 | Kousai et al. | 604/164 |
| 4,748,982 | 6/1988 | Horzewski et al. | 128/344 |
| 4,771,777 | 9/1988 | Horzewski et al. | 128/344 |
| 4,801,294 | 1/1989 | Okada | 604/171 |
| 4,827,941 | 5/1989 | Taylor et al. | 128/657 |
| 4,842,590 | 6/1989 | Tanobe et al. | 604/282 |
| 4,858,810 | 8/1989 | Intekofer et al. | 226/127 |
| 4,863,439 | 9/1989 | Sanderson | 604/93 |
| 4,886,500 | 12/1989 | Lazarus | 128/772 |
| 4,905,667 | 3/1990 | Foerster et al. | 604/280 |
| 4,909,258 | 3/1990 | Kuntz et al. | 128/658 |
| 4,929,236 | 5/1990 | Sampson | 604/175 |
| 4,932,413 | 6/1990 | Shockey | 128/657 |
| 4,944,740 | 7/1990 | Buchbinder et al. | 606/194 |
| 4,947,864 | 8/1990 | Shockey | 128/772 |
| 4,969,890 | 11/1990 | Sugita et al. | 606/192 |
| 4,976,689 | 12/1990 | Buchbinder et al. | 604/95 |
| 4,988,356 | 1/1991 | Crittenden et al. | 606/192 |
| 4,994,027 | 2/1991 | Farrell | 604/53 |
| 4,998,923 | 3/1991 | Sampson et al. | 606/194 |
| 5,002,559 | 3/1991 | Tower | 128/772 |
| 5,035,686 | 7/1991 | Crittenden et al. | 604/96 |
| 5,078,702 | 1/1992 | Pomeranz | 604/282 |
| 5,120,323 | 6/1992 | Shockey et al. | 604/282 |
| 5,135,535 | 8/1992 | Kramer | 604/194 |
| 5,147,377 | 9/1992 | Sahota | 128/772 |
| 5,178,608 | 1/1993 | Winters | 604/101 |

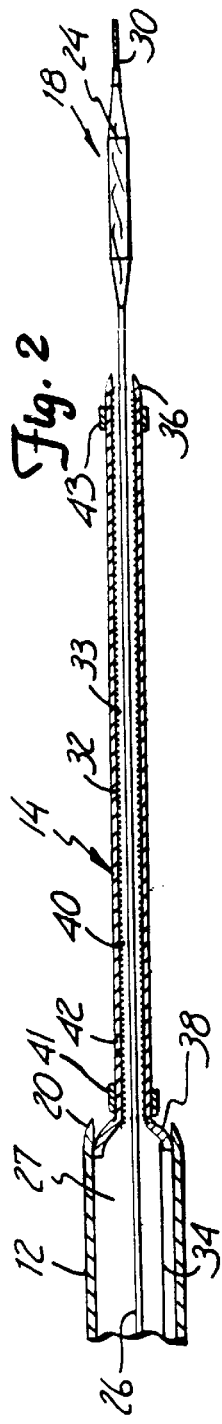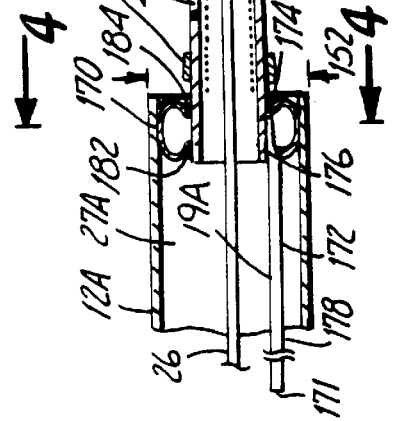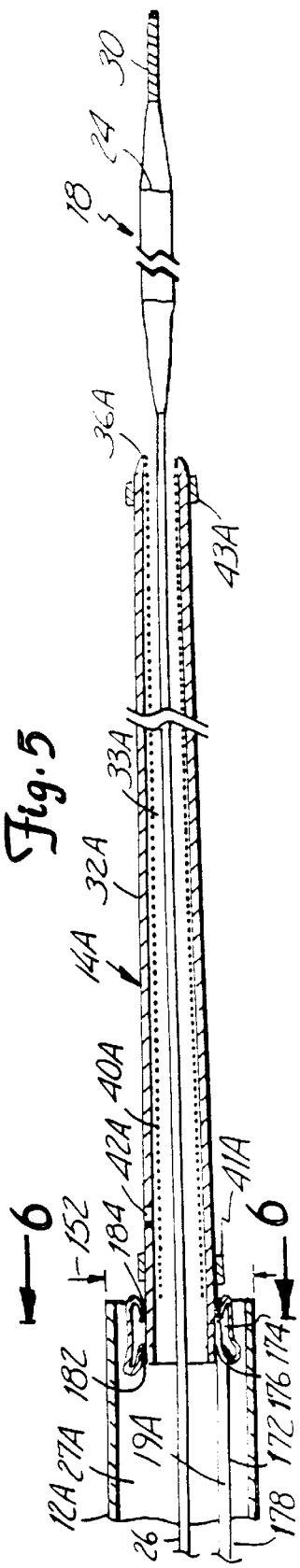

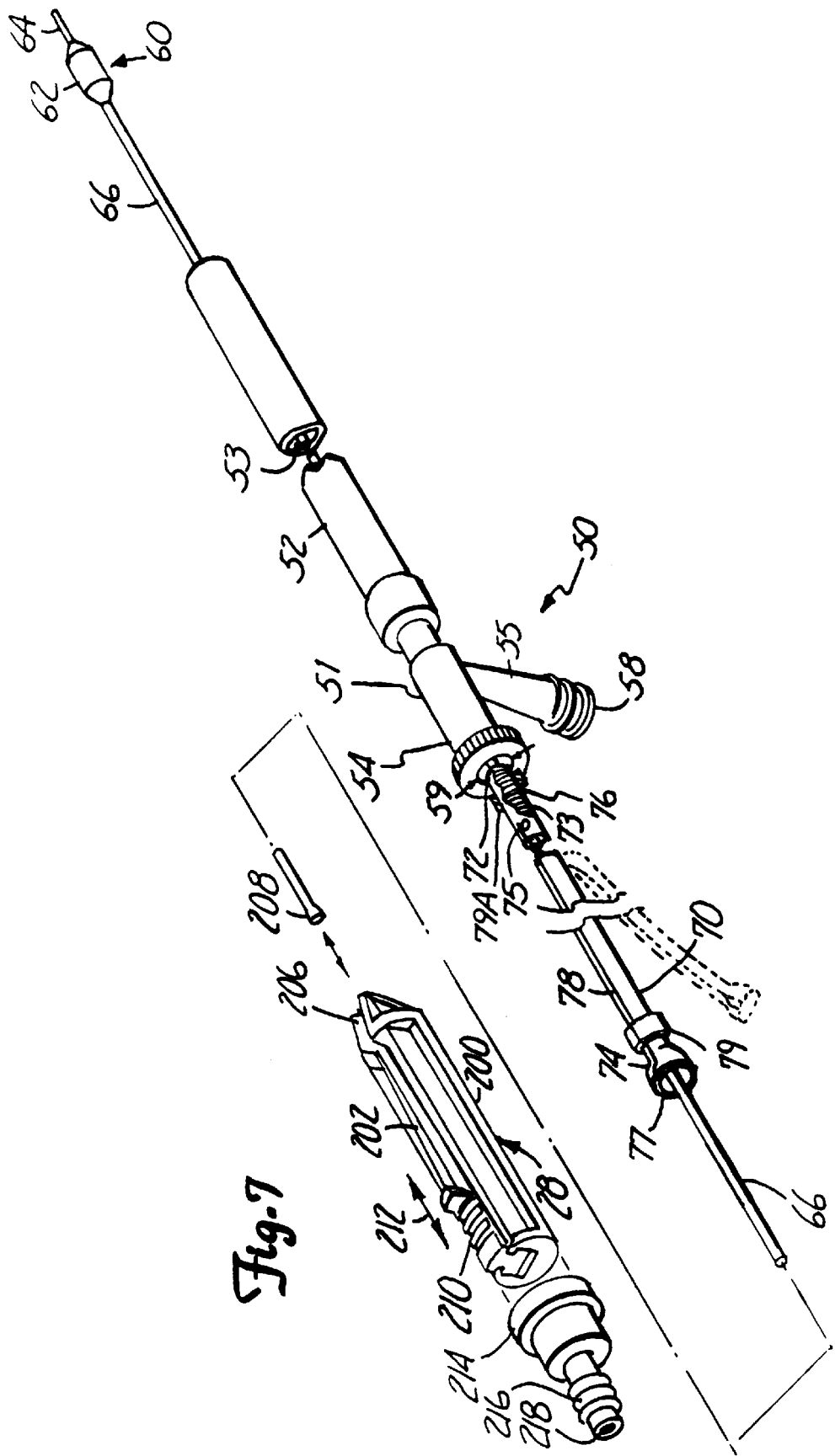

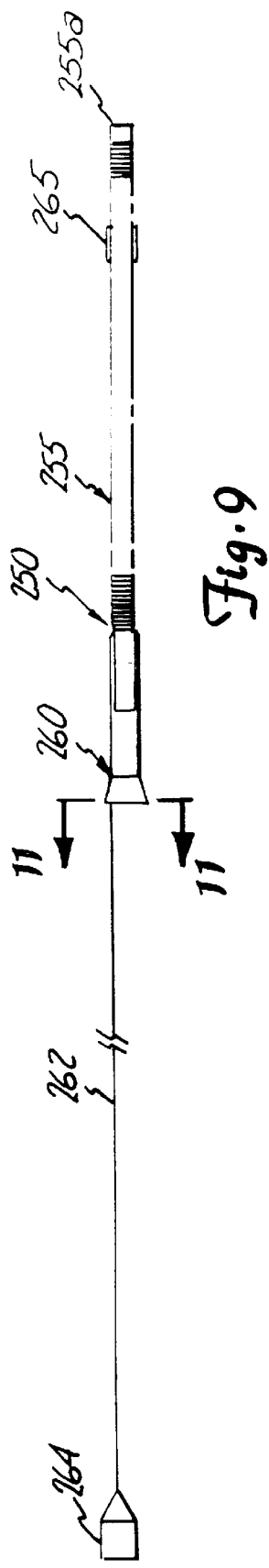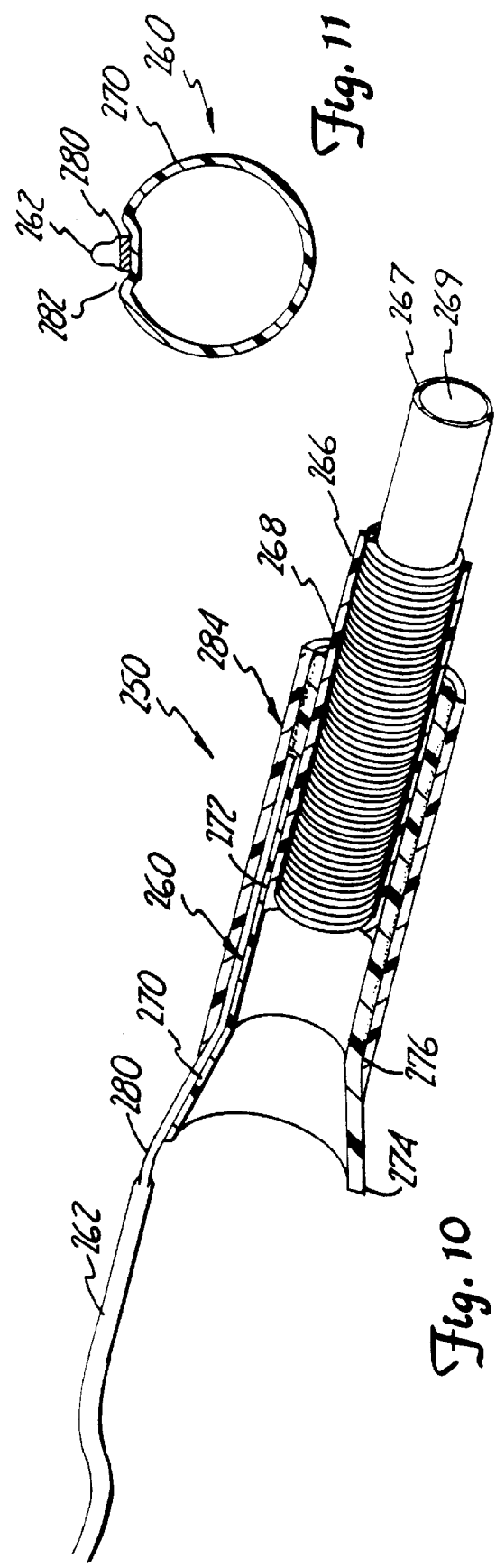

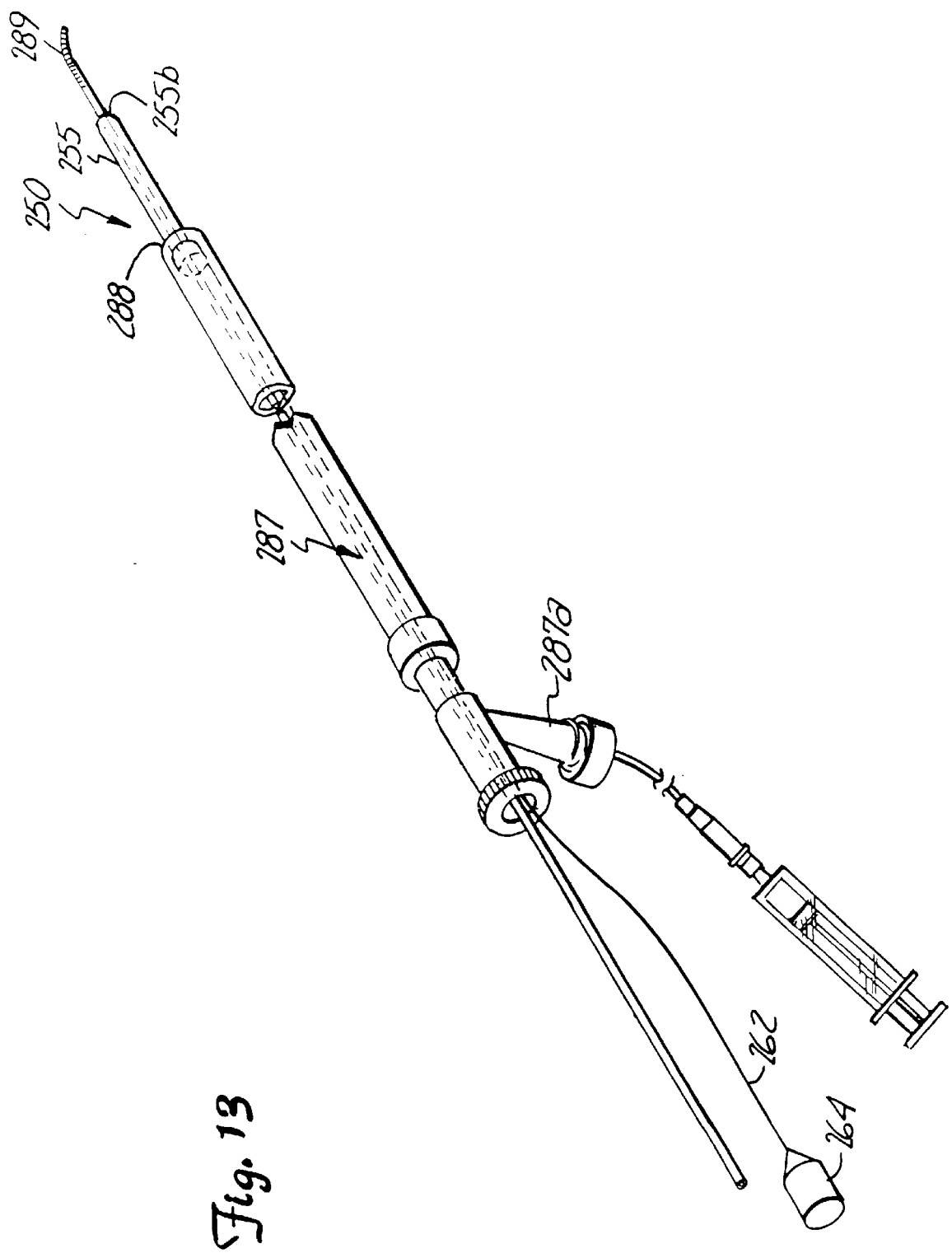

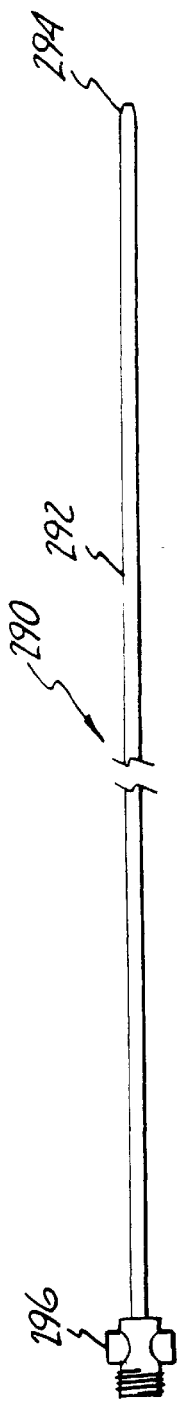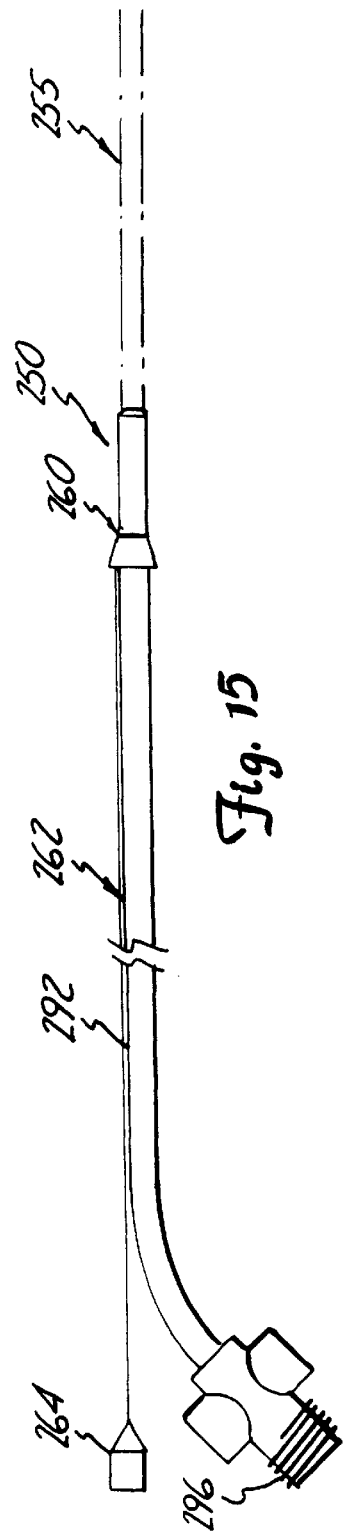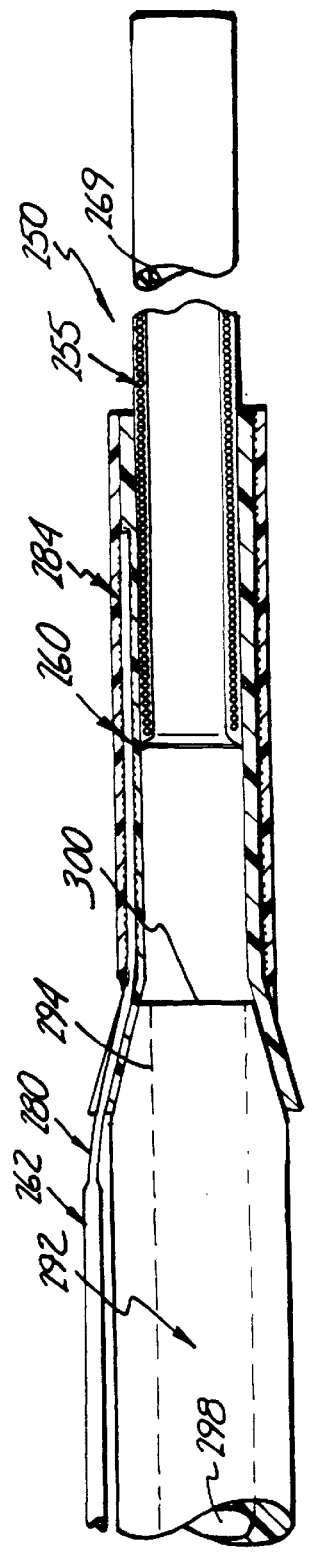

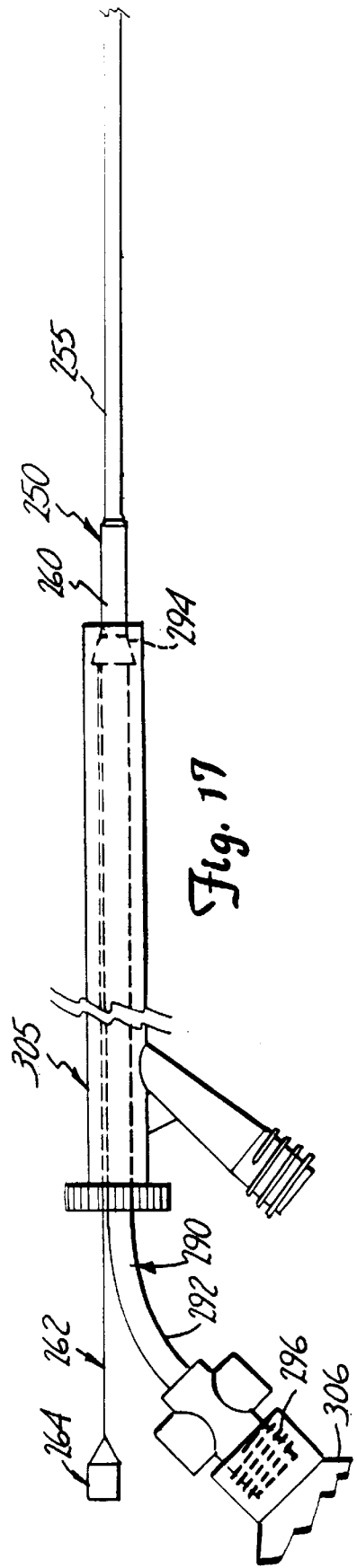

INTRAVASCULAR DEVICE FOR CORONARY HEART TREATMENT

This is a divisional of application Ser. No. 08/303,590, filed Sep. 9, 1994, now U.S. Pat. No. 5,527,292, which is a continuation of application Ser. No. 07/874,079, filed Apr. 24, 1992, now abandoned, which is a continuation-in-part of application Ser. No. 07/605,398, filed Oct. 29, 1990, now abandoned. Priority of the prior application is claimed pursuant to 35 USC § 120.

BACKGROUND OF THE INVENTION

The present invention relates to the field of treatment of heart disease. In particular, the present invention relates to an intravascular device, particularly suited for use for percutaneous transluminal treatment for heart disease.

A normal artery is composed of essentially, three layers, the intima, the media and the adventitia. The intima is the innermost layer of the artery. It is composed of a thin layer endothelial cells that provide a smooth surface between the blood and an interior wall of the artery. The media is an intermediate layer which is separated from the media by an internal elastic membrane, which allows material to diffuse through the intima and into the medial tissue. The media is a muscle layer composed of a network of smooth muscle cells. The smooth muscle cells of the media contract and relax to regulate vessel tone which in turn affects blood pressure and local blood flow. The outermost layer or adventitia is composed of a connective tissue and scattered smooth muscle cell bundles.

Atherosclerosis is a disease which affects a normal artery restricting the function of the artery. Atherosclerosis involves the gradual build up over time of atherocelerotic plaque or atheroma. Atherocelerotic plaque buildup begins in the intimal layer of the artery and progresses with the deposit of fatty debris from the blood through the endothelium. As the formation progresses, the endothelium becomes irregular and the artery constricts because of the build up of the plaque. The build up is so significant that the plaque now diminishes the effectiveness or area of the artery.

Balloon dilatation angioplasty has become recognized as an efficient and effective method for treating atherocelerotic buildup in coronary arteries. A dilatation balloon catheter is inserted preferably into the femoral artery of the patient and it is advanced to the obstructed area of the coronary artery. The balloon is inflated to compress the plaque against the artery wall and also to stretch the artery to dissect the plaque and open the artery thereby permitting an acceptable artery blood flow.

Before an angioplasty procedure is performed, radiography is used to survey the extent of damage or disease present in the artery. Dilatation balloon catheters are rated for different functions depending on the extent to which the artery is occluded or obstructed by plaque and the stage to which the atherocelrotic deterioration has progressed.

However, often times, the nature and extent of the damage is not apparent from the pre-angioplasty analysis and it is necessary to substitute the original balloon catheter inserted for an alternate sized balloon catheter. This process is generally referred to as a catheter exchange. A catheter exchange becomes a very arduous procedure if it is necessary to retrace the second catheter through the tortious anatomy (i.e., through a coronary artery) of a patient to position the balloon at the occluded area.

There are generally two type of balloon catheters, over-the-wire catheters and non-over-the wire-type catheters. In an over-the-wire catheter, the wire is slidably disposed within the catheter so that the catheter may be withdrawn independently of the wire, and the wire can remain in place to guide a substitute catheter to the treatment site. In a non-over-the-wire catheter the entire catheter is withdrawn during a catheter exchange so the tortious path to the treatment site must be retraced.

The condition of the patient may also be affected by thrombolytic buildup which can also occlude the lumen of the artery. Thrombolytic buildup results from platelet found in red blood cells which is thought to promote coagulation. In a healthy artery, endothohelial cells produce substances that inhibit platelet. Thus, there is a propensity for thrombolytic buildup at the diseased site in an artery. Further stagnation of the blood flow and platelet during angioplasty increases the risk of thrombolytic buildup.

Thrombolytic drugs and agents are generally used to dissolve the blood clot caused by the "build up" of platelet matter and to reverse the build up of the platelet matter. Alternatively, aspiration is another technique for treating thrombus "build up". It is important that the thrombolytic drugs or other treatment be administered before blood flow through the artery is completely or significantly restricted. Furthermore, thrombolytic drugs are generally extremely expensive so it is desirable that the drug be administered effectively and efficiently without waste.

Accordingly, it is important to be able to selectively provide a means for efficiently introducing a thrombolytic agent into the diseased artery during a balloon dilatation procedure. Also, if necessary it is desirable to be able to easily substitute one size catheter for a different size catheter if the original catheter inserted can not properly dilate the lesion.

SUMMARY OF THE INVENTION

The present invention relates to a catheter system for treating coronary heart disease. In particular, the present invention relates to an intravascular device suited for use during angioplasty treatment. The device is sized for insertion through a coronary arteries to reach an occluded area for treatment. Although use of the device is explained with reference for treating coronary arteries it should be understood that the device may also be used for treating other diseased vessel in a patient.

The intravascular device includes a relatively flexible tube having a proximal and a distal end. The tube is designed to extend from a distal end of a guide catheter through a coronary artery requiring treatment. A push rod is attached to a proximal end of the tube for slidably positioning the tube beyond a distal end of a guide catheter into and through the artery. The flexible tube has an inner diameter sized for insertion over an angioplasty device.

The tube of the intravascular device has sufficient flexibility to provide for trackability of the flexible tube through the tortuous coronary arteries. Thus, the relatively flexible tube may be advanced into a artery until the distal end thereof is positioned at a treatment site.

Since the tube is flexible, the tube is not very pushable. The flexible tube may be advanced over an angioplasty balloon catheter or other coronary treatment device to provide pushability for placement of the flexible tube through the artery. The inner diameter of the flexible tube is larger than the outer diameter of a typical angioplasty balloon catheter or other coronary treatment device.

It is contemplated, that the intravascular device may be used for the placement of an angioplasty balloon catheter or alternatively a guide wire into a coronary artery requiring treatment. Furthermore, the intravascular device is particularly suited for use during a catheter exchange or a guide wire exchange.

Also the intravascular device may be used for drug treatment to relieve thrombolytic build-up in a coronary artery. Since the intravascular device is inserted into and through the coronary artery, it provides a conduit for drug delivery thereto. Thrombolytic drugs may be delivered to a treatment site in combination with a guide catheter and the intravascular device. Additionally, the drugs may be delivered in combination with a proximal drug delivery attachment. The proximal drug delivery attachment includes an elongated attachment tube designed for placement through a guide catheter. The drug delivery attachment also includes a coupling means for fluidly sealing the attachment tube relative to the proximal end of the intravascular device to define a continuous lumen therealong for drug delivery.

In addition, the intravascular device may be used for aspirating thrombus from a coronary vessel. Again, since the intravascular device is inserted into and through the coronary vessel requiring treatment, the intravascular device provides a conduit, in combination with a guide catheter, for pulling a net negative pressure for withdrawing thrombus from the vessel. Alternatively, net negative pressure may be applied in combination with a proximal attachment tube and the intravascular device for aspiration treatment.

BRIEF DESCRIPTION OF THE DRAWINGS

The invention will be further described with reference to the accompanying drawings where like numbers refer to like parts in several views and wherein:

FIG. 2 is a transverse view in partial cross section of one embodiment of the guide catheter extension tube (distal extension) of FIG. 1.

FIG. 3 is a transverse view in partial cross section of another embodiment of the guide catheter extension tube (distal extension) of FIG. 1, the extension tube including a restriction balloon, which is shown in an inflated condition.

FIG. 5 is a transverse view in partial cross section of the guide catheter extension tube (distal extension) of FIG. 3 with the restriction balloon shown in a deflated condition.

FIG. 7 is a broken-away perspective view of another embodiment of the guide catheter system of the present invention with a dilatation balloon shown in an inflated condition.

FIG. 9 is an elevational view of an alternate embodiment of a distal extension (intravascular device), similar to FIGS. 2–6.

FIG. 10 is a perspective view, in partial cross-sectional, of the distal extension of FIG. 9.

FIG. 11 is a cross-sectional view as taken along lines 11—11 of FIG. 9.

FIG. 13 is a broken-away perspective view of a guide catheter system including the distal extension of FIG. 9 for placement of a guide wire.

FIG. 14 is an elevational view of a proximal elongated attachment tube of the present invention.

FIG. 15 is an elevational view of the distal extension (intravascular device) shown coupled with the proximal elongated attachment tube of FIG. 14.

FIG. 16 is a transverse view, in partial cross-section, of the distal extension coupled with the proximal elongated attachment tube of FIG. 14.

FIG. 17 is an elevational view of a guide catheter system including the distal extension (intravascular device) of FIG. 9 and the proximal elongated attachment tube of FIG. 14.

While the above identified drawing figures set forth several preferred embodiments, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

The invention is directed to the structure and use of a distal extension (intravascular device) for a guide catheter. Quite often, after a dilatation balloon catheter is inserted into a patient, it is necessary to withdraw the balloon catheter to substitute an alternate sized balloon catheter. This is done during a catheter exchange. This invention allows relatively easy and accurate exchanges for "non-over-the-wire" catheters, guide wires and other coronary treatment devices and is disclosed in several alternative embodiments.

The distal extension (intravascular device) for the guide catheter disclosed may also be used for drug delivery to a treatment site. The distal extension disclosed has a small outer diameter sized for insertion through the arterial system of a patient beyond a distal end of the guide catheter into a coronary artery. The distal extension is formed of a relatively flexible tube to permit the extension to track through the tortuous coronary arteries to a treatment site. Since the extension reaches a treatment site, it may be used to provide a conduit for applying negative pressure for aspirating thrombus from a diseased coronary vessel.

Specifically, the guide catheter is inserted at the femoral artery and advanced through a patient's arterial system to the coronary ostium of the artery requiring treatment. The construction of the guide catheter (diameter and rigidity) does not permit the guide catheter to advance beyond the ostium into the artery requiring treatment. The distal extension however is designed for insertion through coronary arteries requiring treatment. Thus, the distal extension may be advanced into and through the coronary arteries to the lesion or obstruction to facilitate original placement of angioplasty devices by serving to anchor the guide catheter at the coronary ostium of the vessel requiring treatment for placement of an angioplasty device or other coronary treatment device into the vessel (e.g., guide wire placement and angioplasty balloon catheter placement) and to provide a less difficult means for performing guide wire exchanges and "non-over-the-wire" catheter exchanges and alternately to provide a means for delivering drugs or providing negative pressure to a treatment site.

Figure 1:
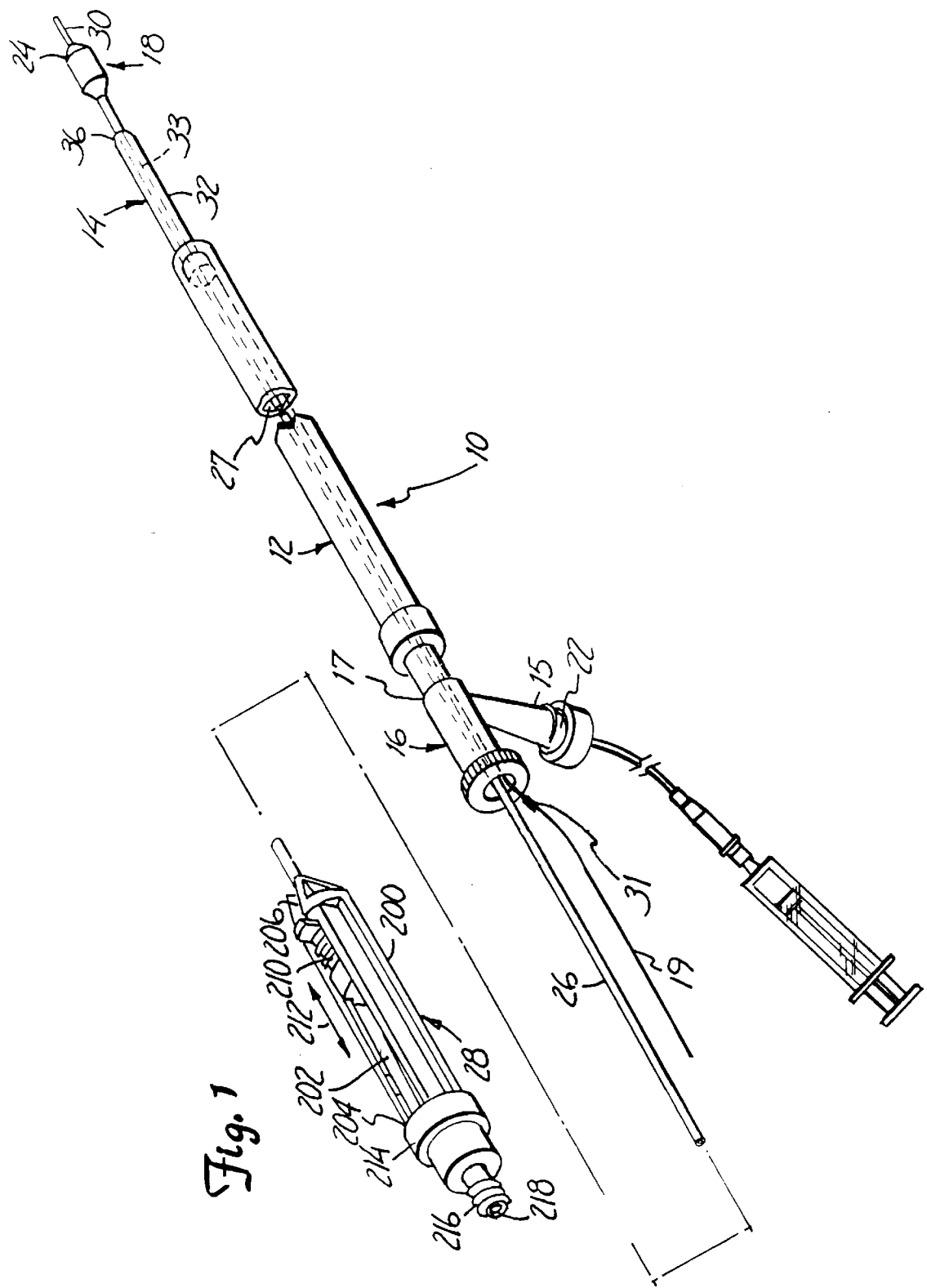
FIG. 1 is a broken-away perspective view of an embodiment of the guide catheter system of the present invention shown with a dilatation balloon in an inflated position.

It is understood that the embodiments of the present invention are illustrative, and should not be construed to limit the scope of the invention. In a first embodiment the distal extension (intravascular device) is shown in association with a guide catheter system 10 (FIG. 1). The guide catheter system 10 includes a guide catheter 12, a guide catheter extension 14 and a guide catheter manifold 16 (FIG. 1).

The guide catheter manifold 16 is mounted at the proximal end of the guide catheter 12. Preferably, the guide catheter manifold 16 comprises a Y-shaped structure having a primary channel leg 17 and an extension leg 15 with a guide catheter port 22 on the extension leg 15. The guide catheter port 22 provides an inlet injection port into the guide catheter 12. Dye is injected into port 22, (from a fluid source—such as a syringe) and travels through the guide catheter system 10 to reach the stenosis. Alternatively, port 22 may be used to introduce drugs (i.e., thrombolytic drugs) through the guide catheter 12 or to apply negative pressure for aspiration. A hemostasis valve (not shown) on channel leg 17 provides hemostatic control for the guide catheter system 10 of the present invention.

The guide catheter 12 is an elongated, flexible, tubular member defining a first guide catheter lumen 27 therethrough. Guide catheter 12 is preferably formed of a polyurethane tube. The guide catheter 12 may be preformed in various shapes to facilitate its passage to the coronary ostium or region within the body where the stenosis is located.

The guide catheter extension (distal extension) 14 comprises an elongated flexible tube 32 defining a second guide catheter lumen 33 and a shaft 19 or a push rod. The elongated flexible tube 32 is preferably formed from a soft, flexible material such as polyolefin, polyethylene or polyurethane and has a rounded distal tip 36 to facilitate insertion and trackability through the coronary arteries. The tube 32 may be loaded with barium sulfate or other suitable material to provide radiopacity. The inner surface of the elongated flexible tube is coated with silicone to provide a slippery surface. Preferably, the elongated flexible tube 32 is formed of a coil spring 40 made from stainless steel or a platinum alloy to provide radiopacity under fluoroscopy (see FIG. 2). An outer coating of plastic is then added around the coil spring 40 using a heat shrink or some similar manufacturing technique to define the tube 32.

If desired, the elongated flexible tube 32 may include one or more holes 42 (FIG. 2) in the sidewall thereof to facilitate the passage of dye from the elongated flexible tube 32 into the artery and to also allow blood from the artery to flow into and through lumen 33 and out the distal end to facilitate distal artery perfusion. However, holes 42 prohibit use of the tube 32 as a drug delivery device for transport of drugs into the coronary arteries to a treatment site. The length of the elongated flexible tube 32 is preferably approximately 6 to 10 inches.

The outer diameter of the elongated flexible tube 32 is smaller than the first guide catheter lumen 27 defined by the guide catheter 12 so that it may be slidably disposed therethrough and to permit insertion of the tube 32 into the coronary arteries. As seen in FIG. 1, shaft 19 or push rod is attached to a proximal end of the elongated flexible tube 32 and extends proximally therefrom outside the guide catheter 12 so that it is accessible to the user. The shaft 19 allows the user to position the guide catheter extension 14 (distal extension) within the patient by either extending or retracting the length of the shaft 19 to advance the guide catheter extension 14 as necessary. The elongated flexible tube 32 of the guide catheter extension 14 is designed to extend beyond a distal end of the guide catheter 12 into the coronary arteries.

Alternate embodiments for a guide catheter extension (distal extension) having an elongated flexible tube and a shaft attached thereto are shown in FIGS. 2–6. One embodiment is shown in FIG. 2, and the shaft 19 or push rod is defined by an elongated wire 34. The elongated wire 34 is of small diameter, preferably 0.010 to 0.016 of an inch in diameter. As discussed, the length of the elongated wire 34 is designed to extend from the elongated flexible tube 32 outside the patient so that it is accessible to the doctor or other user. Accessibility of the elongated wire 34 permits the doctor to adjust the extension length of the flexible tube 32 relative to the guide catheter 12 to position the flexible tube 32 in the coronary arteries.

In the embodiment shown in FIG. 2, the elongated tube 32 has a radially flared proximal end 38. The flared proximal end 38 of the elongated flexible tube 32 is configured to coincide with the inner diameter of the guide catheter 12 so that a catheter advanced, or other angioplasty device such as a guide wire, into and through the first guide catheter lumen 27 is piloted into the flared tip 38 and second guide catheter lumen 33. The close fit of the flared proximal end 38 to the inner diameter of the first guide catheter lumen 27 also directs fluid (such as dye or drugs for treatment) injected into the guide catheter 12 through the second guide catheter lumen 33 of the guide catheter extension 32. The extension length of the elongated flexible tube 32 is lengthened by advancing the wire 34 distally into the guide catheter 12 and into the patient. The length of the flexible tube 32 may be completely extended by advancing the elongated 34 wire until the flared proximal end 38 of the guide catheter extension 14 is just proximal to a distal tip 20 of the guide catheter 12.

An optional radiopaque marker 41 of a platinum alloy may be placed on the proximal end of the extension tube 32 just distal to the flared proximal end 38 to give fluoroscopic imaging of the position of the flared proximal end 38 of the tube 32 relative to the distal tip 20 of the guide catheter 12. Additionally, a radiopaque marker 43 may be placed just proximal to the rounded distal tip 36 of the guide catheter extension tube 32 to located the distal end thereof during operation. Another alternative is to place a visual mark 31 (FIG. 1) on shaft 19 outside the body that indicates a maximum advancement position of the extension tube 32 to prevent passage of the flared proximal end 38 beyond the distal tip 20 of the guide catheter 12.

The use of the elongated wire 34 to adjust the extension length of the elongated flexible tube 32 provides several advantages. The rather thin dimension of the wire 34 eliminates or substantially reduces surface friction introduced by the longitudinal movement of an element within the guide catheter 12. Reduced frictional force allows greater ease in extending and retrieving the guide catheter extension 14. Also, the thin diameter of the wire 34 does not significantly interfere with the flow of dye or other fluid through the guide catheter 12.

Alternatively, there is shown in FIGS. 3–6 another embodiment of a guide catheter extension 14A (distal extension) having an elongated flexible tube 32A connected to a shaft 19A or push rod. The guide catheter extension 14A is operable with a guide catheter 12A which has a longitudinal guide catheter lumen 27A. The guide catheter extension 14A in turn has a longitudinal guide catheter extension lumen 33A therethrough, a rounded distal tip 36A and may be reinforced by a coil 40A. If desired, one or more holes 42A are provided for dye introduction and distal blood perfusion. Also, radiopaque markers 41A and 43A are included at the proximal and distal ends of the tube 32A respectively to provide fluoroscopic imaging of the position of the tube 32A relative to the guide catheter 12A.

The shaft 19A or push rod in this embodiment comprises a tubular shaft member 172 which extends proximally from a proximal end of the elongated flexible tube 32A outside the patient so that it is accessible to the user to continually adjust the extended length of the elongated flexible tube 32A relative to the guide catheter 12A. The tubular shaft member 172 is preferably formed from stainless steel hypotube with an inside diameter of 0.010 inch and an outside diameter of 0.016 inch.

Figure 6:
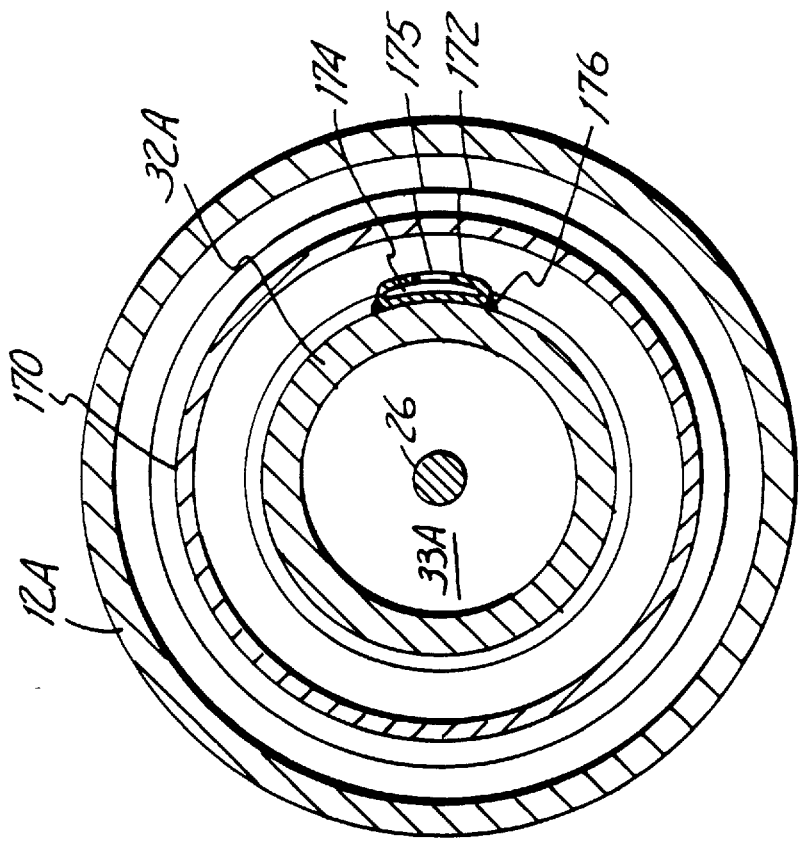
FIG. 6 is a sectional view as taken on line 6—6 of FIG. 5 showing the restriction balloon in a deflated condition.
Figure 4:
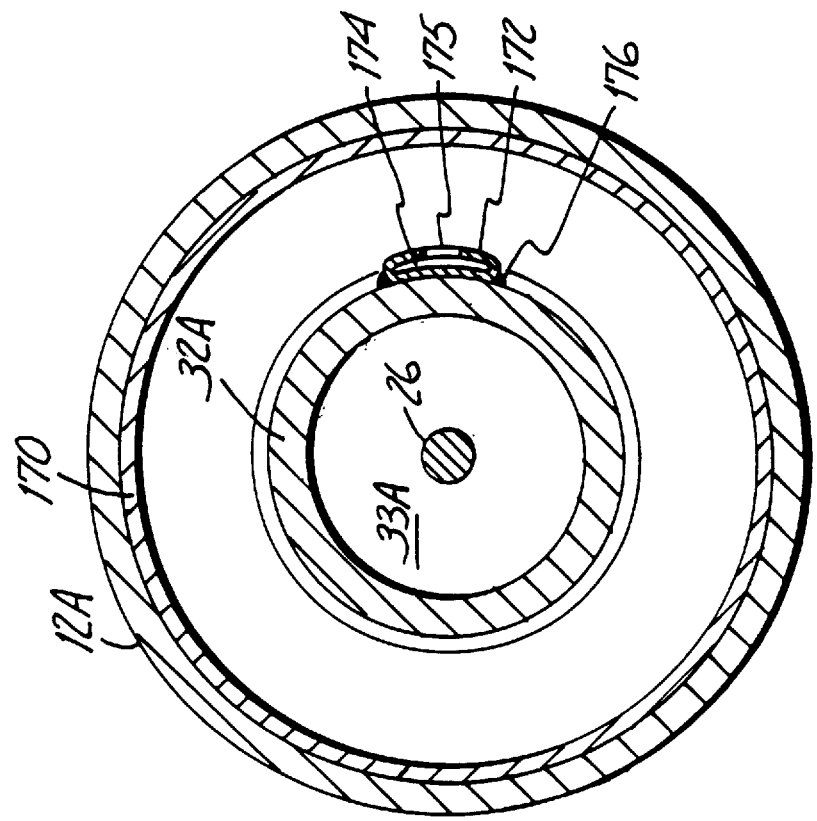
FIG. 4 is a sectional view as taken on line 4—4 of FIG. 3 showing the restriction balloon in an inflated condition.

The tubular shaft member 172 has a flattened distal end which assumes an elongated cross-section as shown in FIGS. 4 and 6. The flattened distal end provides sufficient surface area to secure the tubular shaft member 172 to the proximal end of the elongated flexible tube 32A, preferably by an epoxy bond 176. The tubular shaft member 172 includes a proximally placed inlet port 171 (FIG. 3) which is mounted to a luer fitting (not shown), a distally placed outlet port 174 defined by the flattened cross-section and an inflation lumen 178 therethrough. One or more side holes 175 (FIGS. 4 and 6) may be included to define additional distal outlet ports for the tubular shaft member 172.

An expandable restriction balloon 170 is wrapped about the proximal end of the elongated flexible tube 32A. The restriction balloon 170 extends around the proximal end of the elongated flexible tube 32A as well as the flattened distal end of the tubular shaft member 172 attached to the elongated flexible tube 32A. The restriction balloon 170 is bonded to the elongated flexible tube 32A and the tubular shaft member 172 by a proximal annular bond 182 and a distal annular bond 184. The restriction balloon 170 is preferably formed of a polyolefin. Its position about the flattened distal end of the tubular shaft member 172 and side holes 175 (if included) places the restriction balloon 170 in fluid communication with the inflation lumen 178 of the tubular shaft member 172. The inlet port 171 of the tubular shaft member 172 is connected to an inflation device (not shown) which provides inflation medium to inflate the restriction balloon 170 connected thereto.

In operation, the restriction balloon 170 is inflated to press against an inner surface wall of the guide catheter 12A. The friction caused by the restriction balloon's 170 interaction with the inner surface wall of the guide catheter 12A serves to inhibit longitudinal movement of the elongated flexible tube 32A through the guide catheter lumen 27A of guide catheter 12A. Accordingly, when the extension length of the elongated flexible tube 32A is properly positioned, the restriction balloon 170 is inflated to prohibit the retraction or advancement of the elongated flexible tube 32A through a distal opening 152 of the guide catheter 12A to hold the elongated flexible tube 32A in position during a catheter exchange procedure or while the extension is in use as a drug delivery device (FIGS. 3 and 4).

Alternatively, when the restriction balloon 170 is deflated (FIGS. 5 and 6), it no longer restricts movement of the elongated flexible tube 32A relative to the guide catheter 12A. Thus, the elongated flexible tube 32A may be slidably withdrawn through the guide catheter 12A when its extension beyond the guide catheter 12A is no longer needed. Thus, as described, the restriction balloon 170 provides sufficient friction to maintain a consistent extension length for the elongated flexible tube 32A. The restriction balloon 170 is also adapted in a relaxed position to permit the continued adjustment of the elongated flexible tube 32A within the guide catheter 12A. The deflated balloon has a shape (FIGS. 5 and 6) at the proximal end to facilitate guidance of a catheter 18 advanced through guide catheter lumen 27A into the guide catheter extension lumen 33A of the extension tube 14A or to provide a fluid seal for drug delivery. Thus, the embodiment in FIGS. 3–6 provides an alternative arrangement to that shown in FIG. 2 for controlling the extension length of the elongated flexible tube 32A relative to the guide catheter 12A.

The elongated flexible tube 32A of the embodiment shown in FIGS. 3–6 may be tapered to provide a small diameter section at its distal end to facilitate insertion through the smaller dimension coronary arteries, while maintaining a larger diameter proximal section to correspond to the distal opening 152 of the guide catheter 12A. For example, the outer diameter of the elongated tube 32A at its proximal end would be approximately 0.065 inch and the outer diameter at its distal end would be approximately 0.053 inch (with a 0.045 inch distal tubular opening), the difference defining a gradual taper extending from the proximal end to the distal end of the tube 32A (which is approximately 6 to 10 inches in length). Preferably, the tube 32A has an interior coating of silicone, polyethylene or polytetraflouroethylene to provide a smooth, slick inner surface.

Referring now to FIGS. 1 and 2, an angioplasty balloon catheter 18 is inserted into a patient's vascular system with the aid of the guide catheter 12 and guide catheter extension 14. The angioplasty balloon catheter 18 includes a balloon 24, a hollow balloon catheter shaft 26 and a balloon inflation assembly 28, with the balloon 24 positioned at the distal end of the hollow balloon catheter shaft 26. The diameter of the first guide catheter lumen 27 in the guide catheter 12 and the second guide catheter lumen 33 in the guide catheter extension 32 are larger than the outer diameters of the hollow balloon catheter shaft 26 and balloon 24 (deflated) which are advanced therethrough. A flexible spring tip 30 is mounted at the distal end of the balloon 24, and generally assists the insertion of the balloon catheter 18 through the arterial system.

The balloon inflation assembly 28 (FIG. 1) is mounted at a proximal end of the hollow balloon catheter shaft 26 and includes an inlet 218 thereon. Inflation medium (from an inflation device—not shown) is injected through the hollow balloon catheter shaft 26 to inflate the balloon 24 mounted at the end thereof.

In operation, the guide catheter 12 is inserted into a patient's arterial system and is advanced therethrough to locate the ostium of the arterial system containing the stenosis or obstruction. Thereafter, the angioplasty balloon catheter 18 and guide catheter extension 14 are coaxially positioned within the guide catheter 12 and are advanced therethrough for use. The angioplasty balloon catheter 18 is advanced so that it is positioned proximate to or across the stenosis or obstruction. Ordinarily, the outer diameter of the guide catheter 12 restricts its entry into the smaller coronary arteries and thus the angioplasty balloon catheter 18 must be advanced independently to access and cross the restriction point.

However, in the guide catheter system 10 of the present invention, the angioplasty balloon catheter 18 may be advanced beyond the distal end of the guide catheter 12 proximate to or across the stenosis or obstruction with the assistance of the guide catheter extension 14 by extending the elongated flexible tube 32. The outer diameter of the elongated flexible tube 32 is small enough to permit its insertion into the smaller coronary arteries containing the obstruction and thus provides support or guidance for a non-over-the-wire catheter beyond the end of the guide catheter 12 and as far as the stenosis and beyond.

The extension of the elongated flexible tube 32 into the smaller dimension arteries also serves to maintain the position of the guide catheter 12 at the coronary ostium during operation. In particular, the flexible tube 32 defines an anchoring device for securing the guide catheter 12 for operation. The shaft 19 or push rod is used to advance the flexible tube 32 beyond a distal end of the guide catheter 12 and the coronary ostium into the coronary arteries. A proximal end of the flexible tube 32 is advanced so that a significant portion of the flexible tube 32 extends into the artery beyond the distal end of the guide catheter 12 to secure the guide catheter 12 at the coronary ostium for guiding a coronary treatment device into the arteries beyond as explained in further detail herein in relation to FIG. 12.

Furthermore, as explained the guide catheter extension 14 is useful for performing a "non-over-the wire" catheter exchange. That is, once the balloon 24 is positioned across the stenosis, it often becomes apparent that a catheter exchange is necessary to substitute a larger balloon than the balloon originally inserted to apply sufficient pressure across the stenosis to reestablish an acceptable blood flow. During the catheter exchange, the angioplasty balloon catheter 18 is withdrawn from the patient so that a different diameter angioplasty balloon catheter can be substituted therefor.

The guide catheter extension 14 (distal extension) which is the subject of this invention provides a means for establishing a path proximate to or across the obstruction or stenosis and directing a substitute angioplasty balloon catheter thereto. Before the original angioplasty balloon catheter 18 is withdrawn, the elongated flexible tube 32 is positioned proximate to or across the lesion. This may be accomplished by advancing the shaft 19 (wire 34 in FIG. 2 and tubular shaft member 172 in FIGS. 3 and 5) distally within the guide catheter 12 to position the elongated flexible tube 32 proximate to or across the lesion. Then, the original angioplasty balloon catheter 18 is withdrawn and the new angioplasty balloon catheter is substituted therefor. During the insertion thereof, the guide catheter 12 and the guide catheter extension 14 cooperate to direct the new angioplasty balloon catheter to the stenosis.

If it was not anticipated that a catheter exchange would be necessary and the guide catheter extension 14 was not pre-loaded in the guide catheter 12 when the original balloon catheter 18 was inserted, the guide catheter extension 14 may be inserted for use by first detaching the balloon inflation assembly 28 and mounting the flexible tube 32 of the guide catheter extension 14 over the catheter shaft 26. The balloon inflation assembly 28 includes a coupler 200 (see FIGS. 1 and 7) having a through slot 202 that extends from a proximal end 204 to a distal end 206 of the coupler 200. The through slot 202 is configured to receive a tubular proximal portion 208 (FIG. 7) of the catheter shaft 26 of the balloon catheter 18.

The coupler 200 further includes a sliding member 210 having a generally planar engagement surface that is aligned parallel to a planar bottom wall of the through slot 202. The sliding member 210 is movable longitudinally along the coupler (as represented by the directional arrow 212) between a first state wherein the engagement surface of the sliding member 210 is spaced from the bottom wall of the through slot 202 such that the proximal portion 208 of the catheter shaft 26 can be readily inserted into the through slot 202 (FIG. 7); and a second state wherein the proximal portion 208 is securely gripped between the engagement surface of the sliding member 210 and the bottom wall of the through slot 202 (FIG. 1). As seen in FIG. 7, the sliding member 210 is in the catheter shaft receiving first state when the sliding member 210 is positioned at the proximal end 204 of the coupler 200. As seen in FIG. 1, the sliding member 210 is in the catheter shaft gripped second state when the sliding member 210 is positioned near the distal end 206 of the coupler 200.

The proximal end 204 of the coupler 200 includes a luer fitting 214 having a threaded portion 216 that is adapted to cooperate with a threaded distal end of an inflation device (not shown). The luer fitting includes a through opening 218 in aligned registry with the through slot 202 of the coupler 200. An annular seal within the through opening 218 receives the proximal portion 208 of the catheter shaft 26 and forms a fluid tight seal between the balloon inflation assembly 28 and the balloon catheter 18 when the proximal portion 208 of the catheter shaft 26 is gripped within the coupler 200. This arrangement permits inflation medium from the inflation device to enter the balloon catheter 18 through the proximal portion 208 and to travel up the catheter shaft 26 to inflate the balloon 24. The balloon inflation assembly 28 as described may be readily attached to and detached from the balloon catheter 18 in the event a catheter exchange is necessary. The coupler 200 is further detailed in a co-pending application filed by the same assignee, SciMed Life Systems, Inc., on Oct. 24, 1990, and entitled "Catheter Exchange Apparatus with Removable Inflation Assembly." The disclosure of this co-pending application, Ser. No. 07/602,759, now abandoned is hereby incorporated by reference into the present application.

Thus, the sliding member 210 is slid towards the proximal end 204 of the coupler 200 (FIG. 7) to release the inflation assembly 28 from the shaft 26. Thereafter, the elongated flexible tube 32 of the guide catheter extension 14 is positioned about the catheter shaft 26 by aligning the distal end of the extension tube 32 over the proximal end of the catheter shaft 26 and coaxially advancing the extension tube 32 therealong. The elongated flexible tube 32 is introduced into the patient and is further advanced until the distal end thereof is positioned about the original angioplasty balloon catheter 18, proximate to or across the stenosis. Once the flexible tube 32 is positioned proximate to or across the stenosis, the original balloon catheter 18 is then withdrawn and an alternate sized angioplasty catheter is inserted therefor. The guide catheter 12 and the flexible tube 32 of the guide catheter extension 14 cooperate to direct the new angioplasty balloon catheter to the previously established position of the stenosis.

With respect to the embodiment of the present invention illustrated in FIGS. 3–6, a catheter exchange is accomplished in a generally similar manner. The angioplasty balloon catheter 18 is advanced distally through the guide catheter 12A and perhaps the guide catheter extension 14A to a desired position across a stenosis. Should a balloon catheter exchange be necessary, the shaft 172 is used to position the flexible tube 32A across or proximal to the stenosis. Once the desired position of the flexible tube 32A is achieved, the restriction balloon 170 is inflated to hold the tube 32A in place during the catheter exchange. The balloon catheter 18 is then withdrawn proximally through lumens 33A and 27A of the guide catheter extension 14A and guide catheter 12A respectively, and another angioplasty balloon catheter is advanced distally through those lumens to a desired position relative to the stenosis. Preferably, the guide catheter extension 14A is flexible enough and small enough in diameter that its distal tip 36A can be positioned adjacent to the stenosis so that a balloon catheter advanced therethrough is "guided" to its destination along nearly the entire path.

FIG. 7 illustrates another embodiment of a guide catheter system 50 of the present invention. The guide catheter system 50 includes a guide catheter 52, a guide catheter extension tube 70 and a guide catheter manifold 54.

Guide catheter 52 is an elongated, flexible tubular member defining a first guide catheter lumen 53 through which an angioplasty balloon catheter 60 or other angioplasty device is disposed and guided to a stenosis or obstruction. The guide catheter manifold 54 is mounted at a proximal end of the guide catheter 52, and preferably comprises a Y-shaped structure having a primary channel leg 51 and an extension leg 55 with a guide catheter port 58. The guide catheter port 58 provides an inlet injection port for dye to travel through the guide catheter system 50 to the arterial system or alternatively for the introduction of drugs into the patient to a treatment site. A hemostatic valve (not shown) on the primary channel leg 51 provides hemostatic control for the guide catheter.

The guide catheter 52 assists the insertion of an angioplasty balloon catheter 60 to the stenosis or lesion. The angioplasty balloon catheter 60 includes a balloon 62, a hollow catheter shaft 66, a balloon inflation assembly 28, and a flexible spring tip 64. The spring tip 64 is disposed at the distal end of the catheter shaft 66 and generally assists the insertion of the angioplasty catheter 60 through the arterial system of a patient.

The balloon inflation assembly 28 is mounted at a proximal end of the hollow catheter shaft 66 and has an inlet port 218 thereon. Inflation medium (from an inflation device—not shown) is injected through the hollow balloon catheter shaft 66 to inflate the balloon 62 mounted at the end thereof.

The guide catheter extension tube 70 defines a second guide catheter lumen 77 and is made from a soft, relatively flexible material such as polyolefin, polyethylene or polyurethane. The guide catheter extension tube 70 has a reinforced flexible distal end portion 73, a rounded distal tip 72 and a flared proximal end 74. The reinforced distal end portion 73 of the guide catheter extension tube 70 is formed from a coated or sheathed wire coil 76 to provide flexibility and pushability therefor. One or more side holes 75 may be added in the distal end portion 73 for distal blood perfusion. The outside diameter of the guide catheter extension tube 70 is smaller than the inside diameter of the guide catheter 52 such that the guide catheter extension tube 70 may be inserted and slidably disposed therethrough. During use, the guide catheter extension tube 70 is coaxially disposed within the guide catheter 52. The guide catheter extension tube 70 is longer than the guide catheter 52 so that a portion of the extension tube 70 extends beyond the distal end of the guide catheter 52 to bridge the gap between the distal end of the guide catheter 52 and the stenosis or obstruction.

The guide catheter extension tube 70 also includes a longitudinal slit 78 that extends from a proximal end of the reinforced distal end portion 73 to the flared proximal end 74. The reinforced distal end portion 73 defines a rigid portion that may be mounted about the proximal end of the catheter shaft 66 and supported thereby prior to use of the extension tube 70. This pre-use position of the reinforced distal end 73 and the extension tube 70 is depicted by the phantom line drawing in FIG. 7. As shown, the slit 78 is formed to be normally resiliently closed but, it may be forcibly "peeled" opened to position the remaining length of the extension tube 70 (the portion extending from the flared proximal end 74 to the proximal end of the reinforced distal end portion 73) about the catheter shaft 66 for insertion through the guide catheter 52. The reinforced distal end portion 73 may be mounted over the catheter shaft 66 prior to insertion of the catheter 60 to assume the pre-use position depicted by the phantom line drawing in FIG. 7. To position the reinforced distal end portion 73 about the catheter shaft 66 prior to insertion of the catheter 60, the distal end portion 73 is installed over the distal end of the catheter shaft 66 and is advanced towards the proximal end thereof.

Alternatively, the reinforced distal end portion 73 may be mounted over the proximal end of the catheter shaft 66 as needed by detaching (as depicted in FIG. 7) the balloon inflation assembly 28 from the proximal end of the catheter shaft 66. The balloon inflation assembly 28 includes a coupler 200 as previously explained with reference to the balloon inflation assembly 28 (FIG. 1). As described, (FIGS. 1 and 7) the coupler 200 includes a through slot 202 configured to receive a tubular proximal portion 208 of the catheter shaft 66. A sliding member 210 having a generally planar engagement surface is designed to grip the planar bottom wall of the through slot 202 when in an engaged position (in the engaged position the sliding member 210 is positioned near the distal end 206 of the coupler 200 as shown in FIG. 1) to connect the catheter shaft 66 to the inflation assembly 28 for operation. The catheter shaft 66 is released from the inflation assembly 28 by moving the sliding member 210 longitudinally along the coupler towards the proximal end 204 (where the engagement surface of the sliding member 210 is spaced from the bottom wall of the through slot 202). The balloon inflation assembly 28 as described can be readily attached and detached from the catheter shaft 66 in the event a catheter exchange is necessary to position the distal end portion 73 about the proximal portion 208 of the catheter shaft 66 for insertion into the patient.

A luer fitting 214 having a threaded portion 216 is mounted to the proximal end 204 of the coupler to provide an attachment for the inflation device (not shown). The luer fitting 214 includes a through opening 218 in aligned registry with the through slot 202 of the coupler 200. An annular seal within the through opening 218 receives the proximal portion 208 of the catheter shaft 66 and forms a fluid tight seal between the balloon inflation assembly 28 and the balloon catheter 60 when the proximal portion 208 of the catheter shaft 66 is gripped within the coupler 200. This arrangement permits inflation medium from the inflation device to enter the balloon catheter 60 through the proximal portion 208 and to travel up the catheter shaft 66 to inflate the balloon 62.

To facilitate a catheter exchange, the reinforced distal end 73 of the guide catheter extension tube 70 is distally advanced into the guide catheter 52 from its position about the proximal portion of the catheter shaft 66. The slit 78 is forced open to position the remaining length of the extension tube 70 about the catheter shaft 66 for insertion (depicted by the solid line structure, FIG. 7). The guide catheter extension tube 70 is distally advanced until the distal tip 72 is positioned proximate to the stenosis, or until the flared proximal end 74 thereof is just proximal to an opening 59 into the guide catheter 52. The diameter of the flared proximal end 74 of the extension tube 70 is larger than the opening 59 into the guide catheter 52 to prevent the over insertion of the extension tube 70 into the guide catheter 70 so that a portion remains outside the patient for control. The length of the guide catheter extension tube 70 is long enough so that the distal tip 72 reaches the stenosis while a portion of the tube remains outside the patient for control. Further, the diameter of the extension tube 70 is larger than the balloon 62 (deflated) and the catheter shaft 66 so that the angioplasty balloon catheter 60 may be slid therethrough. Radiopaque markers 79 and 79A may be included at the proximal end and the distal end of the guide catheter extension tube 70, respectively, to assist with the insertion of the tube 70 through the patient's artery.

Once the guide catheter extension tube 70 is positioned proximate to or across the stenosis, the angioplasty balloon catheter is withdrawn and an alternate sized angioplasty balloon catheter is substituted therefor. As the new angioplasty balloon catheter is inserted, the guide catheter 52 and guide catheter extension tube 70 cooperate to direct the new angioplasty balloon catheter to the previously established position of the stenosis so that the stenosis may be further treated.

Figure 8:
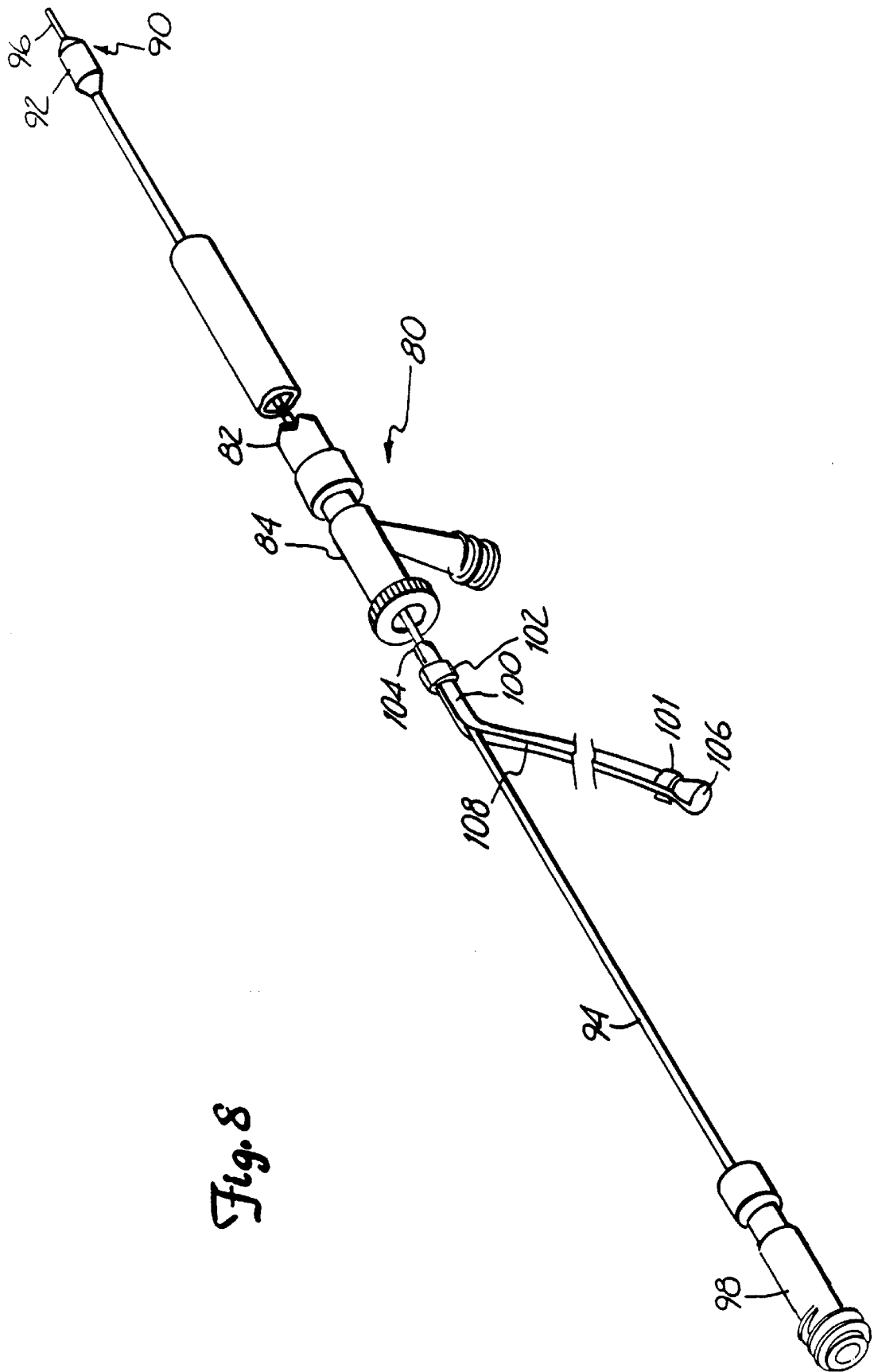
FIG. 8 is a broken-away perspective view of another embodiment of the guide catheter system of the present invention with a dilatation balloon shown in an inflated condition.

FIG. 8 illustrates another embodiment of a guide catheter system 80 of the present invention. As shown in FIG. 8, the guide catheter system 80 has a guide catheter extension tube 100 designed for placement within a guide catheter 82, which is mounted to a guide catheter manifold 84. The guide catheter extension tube 100 includes a longitudinal slit 108 extending its entire length. The extension tube 100 has a rounded distal tip 104 and a flared proximal end 106. The guide catheter extension tube 100 is used in association with an angioplasty catheter 90 having a hollow balloon catheter shaft 94, a balloon inflation assembly 98, a balloon 92 and a flexible spring tip 96. The diameter of the balloon 92 (deflated) and the catheter shaft 94 are small enough so that the catheter 90 may be inserted into and slidably disposed through the extension tube 100.

If a balloon catheter exchange is necessary, the guide catheter extension tube 100 is positioned about the catheter shaft 94, and is inserted through the guide catheter 82. As the extension tube 100 is inserted through the guide catheter 82, the slit 108 is forced open beginning at the distal tip 104 and extending to the flared proximal end 106 to align the extension tube 100 about the catheter shaft 94 for insertion. The extension tube 100 is advanced within the guide catheter 82 until the distal tip 104 thereof is positioned proximate to the stenosis or until the flared proximal end 106 abuts the guide catheter manifold 84. Radiopaque markers 101 and 102 may be included at the proximal end and the distal end of the guide catheter extension tube 100, respectively, to assist the insertion of the tube 100 through the patient's artery. The guide catheter extension tube 100 is longer than the guide catheter 82 to provide sufficient length for the extension tube 100 to extend beyond the distal end of the guide catheter 82 to the obstruction and to provide a portion that remains outside the patient for control (the flared proximal end 106 prevents over-insertion of the extension tube 100 into the guide catheter 82). In this embodiment, the length of the longitudinal slit 108 extends the entire length of the extension tube 100. Thus, the balloon manifold 98 does not need to be removed to position the extension tube 100 about the catheter shaft 94 for insertion into the guide catheter 82.

FIGS. 9–11 illustrate another embodiment of a distal extension 250 similar to that disclosed in FIGS. 1–2. The extension 250 includes a relatively flexible tube 255 having a proximal funnel 260, a push rod 262 and a control knob 264. The push rod 262 is attached to the flexible tube 255 adjacent the proximal funnel 260. The control knob 264 is attached to a proximal end of the push rod 262. Preferably, as shown in FIG. 9, an annular radiopaque marker 265 of platinum alloy is provided at the distal end of the flexible tube 255 to trace the position of the extension 250 via fluoroscopic imaging. The flexible tube 255 preferably has an inner diameter dimension of about 0.046 inches and an outer diameter dimension of about 0.056 inches.

As shown more clearly in FIG. 10, the flexible tube 255 is formed of a coil spring 266 of Type 304 stainless steel and inner and outer polymer layers 267 and 268, respectively to define a lumen 269 therethrough (FIG. 10). Preferably, the coil spring 266 is a flattened ribbon spring formed of a ribbon wire having a 0.002 inch by 0.005 inch cross-section. Each of the inner and outer layers 267 and 268 are polyurethane and are approximately 0.0015 inches thick.

The polyurethane coated coil spring 266 defining the flexible tube 255 is formed using a Teflon® coated cylindrical mandrel having a diameter of 0.046 inches. Teflon® is a registered trademark of E. I. Dupont Corporation of Delaware for polytetrafluorethylene. The mandrel is coated with polyurethane by a solvent dip coating process to form the inner polymer layer 267 of the flexible tube 255. The mandrel is coated until the polyurethane coating on the mandrel is 0.0015 inches thick. The ribbon wire is wrapped around the coated mandrel to form the coil spring 266. The number of wrapping turns per inch of the ribbon wire around the mandrel can vary. One example of a coil spring 266 has 100 turns/per inch of ribbon wire. The mandrel is dip coated again in polyurethane to form a 0.0015 inch thick outer polymer layer 268 enclosing the coil spring 266.

A suitable polyurethane coating is sold under the tradename ESTANE by B. F. Goodrich Company of Akron Ohio. Prior to dip coating the outer layer 268, the radiopaque marker 265 is attached to the ribbon spring so that the marker 265 is encapsulated by the outer polymer layer 268 to provide a relatively smooth outer surface for the flexible tube 255 for insertion. The dip coating process covers the longitudinal length of the ribbon spring as well as the ends so that the ribbon spring is totally encapsulated by a polymer coating. After the dip coating process is complete, the mandrel is removed.

An end tip 255a is formed by wicking cyanoacrylate adhesive between the inner and outer layers 267 and 268 and coil spring 266 to assure that the inner and outer layers 267 and 268 of the tip do not separate from the coil spring 266 as the extension 250 is advanced for use and treatment. A suitable adhesive is LOCTITE PRISM 405 cyanoacrylate, available from Loctite, Corp. (Newington, Conn.).

A hydrophilic polymer coating is added to the inner and outer polyurethane layers 267 and 268 to provide a slipperier surface. The coated coil spring 266 forming the tube 255 is extremely flexible to facilitate trackability through the tortuous coronary arteries. The tube 255 is so flexible that the tube must be inserted with the assistance of another coronary treatment device to provide sufficient pushability.

As shown in FIGS. 10 and 11, the proximal funnel 260 includes a distally tapered frusto-conical portion 270 and an elongated tubular portion 272 having an internal diameter sized to fit over the proximal end of the flexible tube 255. The taper of the frusto-conical portion defines a first proximal outer diameter 274 and a second smaller (distal) outer diameter 276. The elongated tubular portion 272 of the funnel 260 surrounds the proximal end of the flexible tube 255. Preferably, the proximal funnel 260 is formed of a polyolefin material. A suitable polyolefin is available from E. I. DuPont Nemours & Co. (Wilmington, Del.) under the tradename SURYLYN® (8527 POC) Ionomer.

The push rod 262 is preferably formed of a nitinol wire (a nickel-titanium intermetallic compound). The nitinol wire is Teflon® coated. The Teflon® coating provides a lubricous outer surface for the wire. The nitinol construction helps reduce wire kinking as the push rod 262 is manipulated. The control knob 264 is formed of a polycarbonate material and is attached to a proximal end of the push rod 262 to provide a means for manipulating the push rod 262 and the flexible tube 255 for placement of the extension 250.

The push rod 262 is approximately 0.018 to 0.024 inches in diameter. A distal end of the wire is preferably flattened as shown in FIGS. 10 and 11 to define a rectangular cross-section 280 at the distal end thereof. The flattened rectangular cross-section 280 of the push rod 262 provides sufficient attachment surface area to attach the push rod 262 to the proximal funnel 260 and thus to the flexible tube 255 as shown in FIGS. 10 and 11.

As shown in FIG. 11, the frusto-conical portion 270 of the proximal funnel 260 includes a recessed wire channel 282. The flattened distal end of the push rod 280 extends through the recessed wire channel 282 to align the push rod 262 essentially parallel to the flexible tube 255 and the elongated tubular portion 272 of the proximal funnel 260.

An outer bond sleeve 284 (FIG. 10) encloses the elongated tubular portion 272 of the proximal funnel 260 and the push rod 262. The outer bond sleeve 284 is preferably formed of polyolefin material. The proximal funnel 260 and the push rod 262 are secured to the flexible tube 255 of the extension 250 by a suitable wicking adhesive (preferably urethane) between the outer bond sleeve 284 and the flexible tube 255. A suitable urethane adhesive is available from H. B. Fuller & Company of Saint Paul, Minn. (Adhesive No. U.R. 3507).

The urethane adhesive surrounds the push rod 262 and the elongated tubular portion 272 of the proximal funnel 260 between the flexible tube 255 and the outer bond sleeve 284 to secure the proximal funnel 260 and the push rod 262 relative to the flexible tube 255. The bonding arrangement with the outer bonding sleeve 284 provides a smooth outer transitional surface where the proximal funnel 260 and the push rod 262 are bonded to the flexible tube 255.

The flexible tube 255 is approximately 6.0 to 12.0 inches in length, and preferably 9.5 to 10.0 inches in length. The push rod is approximately 40.0 to 45.0 inches in length. The overall length of the extension 250 is preferably 50.5 inches to 51.5 inches.

As explained, the extension 250 is advanced through a guide catheter until a distal end of the tube 255 reaches a treatment site. The length of the tube is sized so that the proximal end (i.e., proximal funnel 260) of the tube 255 is enclosed within the guide catheter while the distal end of the flexible tube 255 reaches a treatment site. The proximal funnel 260 (frusto conical portion 270) is never advanced beyond the distal end of the guide catheter so that a continuous lumen may be defined by the combination of the guide catheter and the flexible tube 255.

The flexible tube 255 of the intravascular device 250 is designed for coaxial placement relative to the guide catheter and the flexible tube and in particular, the proximal funnel 260 is sized to fit through the guide catheter. The first outer diameter 274 of the frusto-conical portion 270 of the proximal funnel 260 coincides with the internal diameter of the guide catheter so that there is a close tolerance therebetween to facilitate the insertion of an angioplasty device through the guide catheter and then through the proximal end of the tube 255. Additionally, the close tolerance provides a seal to facilitate the flow of liquids (such as dye and drugs) through the guide catheter and the tube 255 to a selected treatment site. However, the funnel 260 is sufficiently flexible to allow the extension 250 to be slidably advanced through the guide catheter without significant friction. Thus, the proximal funnel 260 serves to direct an angioplasty device into the lumen 269 of the extension 250, or to provide a distal extension of the lumen of the guide catheter for fluid delivery.

Although, the tube 255 has good trackability, it does not have sufficient pushability to be independently advanced through a coronary artery of a patient. Accordingly, the flexible tube is advanced in cooperation with another coronary treatment device (such as shown in FIG. 1) for placement in the artery. Therefore, the inner diameter of the flexible tube 255 is large enough to be advanced over a treatment device. Examples of a treatment device which could be used to support the flexible tube to provide pushability for advancement include, but are not limited to, an angioplasty balloon catheter (as shown in FIG. 1) or a guide wire.

As previously explained, if a catheter exchange is necessary, the flexible tube 255 can be advanced along an angioplasty balloon catheter to the obstruction. Once the distal end of the flexible tube 255 is positioned adjacent to the obstruction or lesion, the original angioplasty catheter may be withdrawn and a substitute angioplasty catheter inserted therefor.

Figure 12:
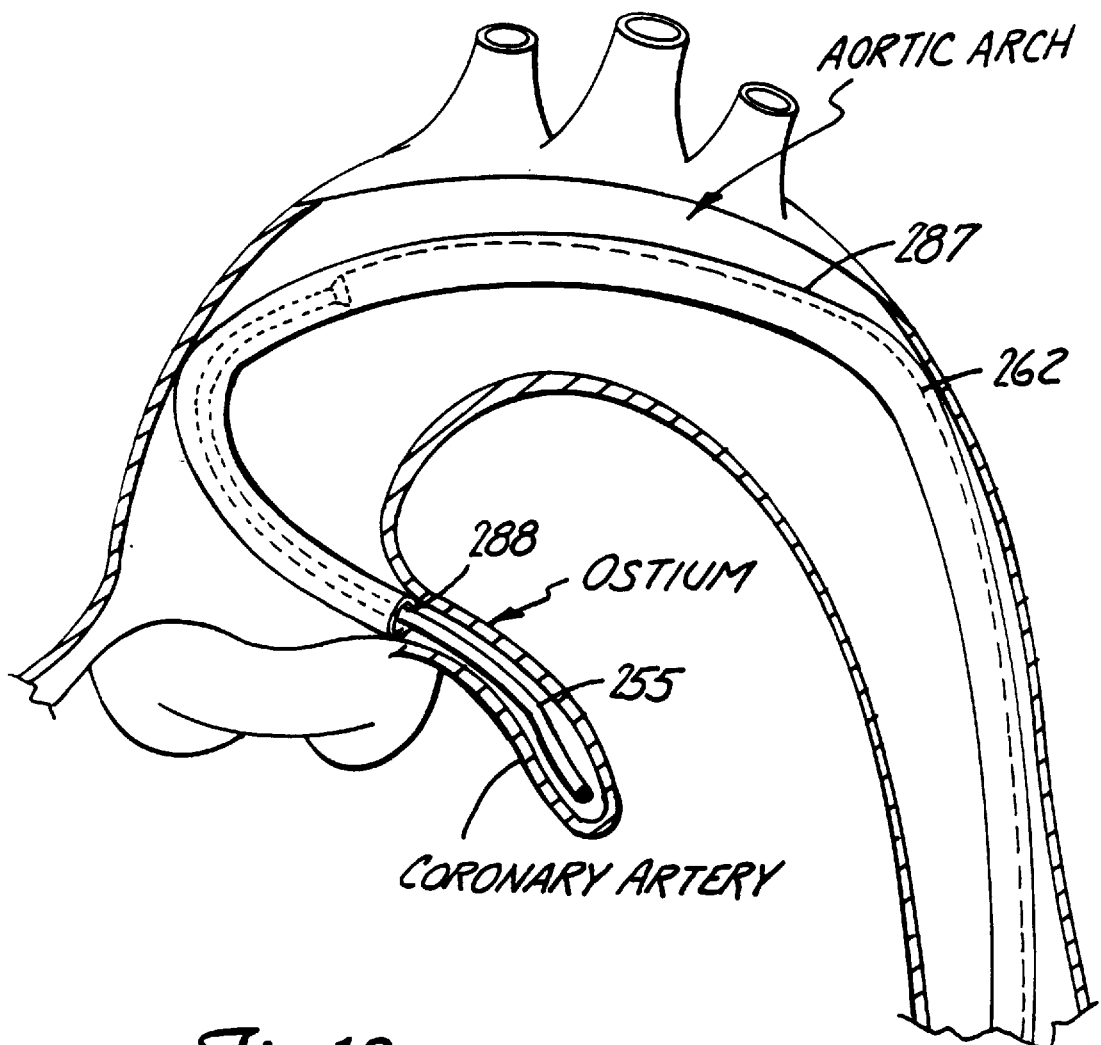
FIG. 12 is an illustrative view of the distal extension of FIG. 9 and the guide catheter relative to the aortic arch, a coronary ostium and coronary artery for placement of angioplasty devices into an occluded vessel for treatment.

As shown in FIG. 12, a guide catheter 287 is inserted into the patient and advanced until a distal end of the guide catheter 287 reaches the aortic arch of the patient. More particularly, the guide catheter 287 is manipulated until a distal opening 288 of the guide catheter 287 is aligned with the coronary ostium so that the guide catheter 287 will direct an original coronary treatment device, such as an angioplasty balloon catheter, or a subsequent coronary treatment device into the coronary artery requiring treatment. It is important that the distal opening 288 of the guide catheter 287 be correctly aligned and that alignment be maintained so the coronary treatment device will be directed through the coronary ostium into the coronary artery requiring treatment. However, as a coronary device is advanced, the position of the distal opening 288 of the guide catheter 287 may shift out of alignment with the coronary ostium making placement of the coronary treatment device into the coronary artery requiring treatment more difficult.

As previously explained, the present invention discloses an anchoring device for securing the guide catheter 287 relative to the coronary ostium of a patient to facilitate original insertion and subsequent insertion of a coronary treatment device. The anchoring device is defined by the flexible tube 255 and push rod 262 (i.e., the distal extension 250). A distal portion of the flexible tube 255 is advanced past the distal opening 288 of the guide catheter 287 and past the coronary ostium into the artery requiring treatment, while a proximal portion thereof and the push rod 262 remain within the guide catheter 287. Since the flexible tube 255 extends along a portion of the guide catheter 287 and through the coronary ostium along an extent of the artery, the flexible tube 255 serves to aid in securing the distal opening 288 of the guide catheter 287 relative to the coronary ostium.

The total length of the extension 250 permits the flexible tube 255 to remain with the guide catheter 287 and to extend beyond a distal end of the guide catheter 287 into and through a coronary artery while the control knob 264 remains outside the patient. The control knob 264 allows the user to control and adjust the position of the extension 250 through the arteries. The outer diameter of the flexible tube 255 is sized so that the flexible tube 255 may be advanced through the coronary arteries, without significant risk of occlusion to the vessel. Further, the flexibility of the tube 255 allows the tube 255 to track through the tortuous coronary arteries.

Alternatively, the extension 250 can be used as a guide wire placement device to assist in the insertion of a typical pre-formed guide wire as generally illustrated in FIG. 13. In particular, the flexible tube 255 and a pre-formed guide wire 289 are cooperatively advanced through the coronary arteries for placement.

Guide wires are pre-formed in generally a J-shape or a straight tip where the practitioner is able to bend the tip to pre-form the wire prior to insertion. A pre-formed guide wire 289 may be advanced through a patient's vascular system within the guide catheter 287 and the flexible tube 255. The pre-formed guide wire 289 is inserted in cooperation with the flexible tube 255 to straighten the guide wire 289 to permit the guide wire 289 and the flexible tube 255 to be advanced into the patient through a coronary artery. The extension 250 is advanced by manipulating the control knob 264 to move the flexible tube 255 through the arterial system of the patient. Thus, the flexible tube 255 straightens the tip of the pre-formed guide wire 289 to allow the guide wire 289 to advance through the patient.

If it is determined that an alternate shaped guide wire is necessary to reach the treatment site, the original guide wire 289 may be withdrawn. The original guide wire 289 is withdrawn through the flexible tube 255 and through the guide catheter 287. An alternate shaped pre-formed guide wire is then inserted in cooperation with the guide catheter 287 and the flexible tube 255 to place the alternative guide wire into a coronary artery for treatment.

Another use for extension 250 is as a drug delivery device. In certain applications, it is useful to be able to provide rapid drug delivery to a treatment area to dissolve thrombolytic buildup caused, inter alia, because of the stagnation of blood flow during an angioplasty procedure. Thus, it is often necessary to provide intermediate drug delivery during an angioplasty procedure to dissolve platelet matter causing thrombolytic buildup. The flexible tube 255 is insertable into the arteries to define a tubular drug delivery extension (or drug deliver device) to provide a conduit for thrombolytic drugs and agents to reach an occluded area in a coronary artery to assure the thrombolytic drug reaches a treatment site.

As previously explained thrombolytic drugs and other liquids,. such as contrast fluid or radiopaque dye may be introduced through a guide catheter (e.g., through port 287a of the guide catheter 287 by a syringe as shown in FIG. 13) for delivery to an occluded coronary artery. The drug flows through the guide catheter 287 and is funneled through the proximal funnel 260 of the extension 250 and then through the flexible tube 255 (i.e., tubular drug deliver extension) to a treatment area. Preferably, drugs or other liquids are introduced through the guide catheter 287 and extension 250 by a 20 cc (cubic centimeters syringe).

The extension 250 may also be used for aspiration to withdraw thrombus from a coronary artery. Net negative pressure is pulled through the guide catheter 287 and the extension 250 via a syringe connected to through port 287a of the guide catheter 287 as shown in FIG. 13 to pull thrombus from the occluded vessel. Preferably a 50 cc (cubic centimeters) syringe is used.

Net negative pressure is applied to move the thrombus toward the extension 250. The thrombus can be removed from the patient in a first manner by aspirating with sufficient force to pull the thrombus toward the extension to "plug" a distal end 255b thereof. Thereafter, the extension 250 is withdrawn from the vessel and the extension 250 is removed from the patient and the thrombus is scraped from the extension 250. Alternatively, sufficient force may be applied to draw ("suck") the thrombus through the extension 250 and the guide catheter for disposal.

Alternatively, as shown in FIGS. 14–17, a proximal elongated attachment tube 290 is designed to couple with the proximal funnel 260 of the distal extension 250 to define a proximal drug delivery attachment. Together, the elongated attachment tube 290 and the distal extension 250 define a continuous conduit for drug delivery. The proximal elongated attachment tube 290 may also define a proximal aspirator attachment to provide a conduit for aspiration in combination with the extension 250. As shown in FIG. 14, the proximal elongated attachment tube 290 includes an elongated flexible tube 292, a distally tapered coupling cone 294 and a proximal luer fitting 296. Preferably, the elongated tube 292 is formed from a polymer tube such as polyethylene.

As shown in FIGS. 15 and 16, the elongated attachment tube 290 is designed to cooperate with the flexible tube 255 of the extension 250 to define a continuous path for drug delivery or aspiration. The coupling cone 294 has a hollow cross-section to define a continuous lumen 298 from the luer fitting 296 to a distal opening 300. The distally tapered coupling cone 294 of the proximal elongated attachment tube 290 is sized for insertion into the distally tapered proximal funnel 260 of the extension 250. Thus, as shown in FIGS. 15 and 16, the distal coupling cone 294 of the proximal elongated attachment tube 290 and the proximal funnel 260 of the distal extension 250 mate so that the continuous lumen 298 of the elongated attachment tube 290 and the lumen 269 through tube 255 are in fluid communication to define a continuous path to a treatment site for drug delivery or for aspiration (i.e., for treatment of a stenosis or obstruction within a coronary artery).

The connection between the coupling cone 294 of the proximal elongated attachment tube 290 and the proximal funnel 260 of the extension 250 is adjusted by manipulating the push rod 262 relative to a proximal end of the elongated attachment tube 290. That is, to provide a tighter relation between the extension 250 and the proximal elongated attachment tube 290, the push rod 262 is moved by the user proximally while the attachment tube 290 is moved distally to force the coupling cone 294 and the proximal funnel 260 in tight relation to provide a tighter fluid connection therebetween.

As shown in FIG. 17, the tube 292 of the proximal attachment tube 290 is sized for insertion through a guide catheter 305. In use, the flexible tube 255 of the extension 250 is inserted into the coronary artery requiring treatment until a distal end reaches the occluded or treatment area. If drug treatment or aspiration is necessary, the proximal attachment tube 290 may be inserted and advanced through the guide catheter 305 so that the coupling cone 294 mates with the proximal funnel 260 of the distal extension 250.

Typically an angioplasty balloon catheter or other coronary treatment device was previously inserted into the patient for treatment or was inserted for placement of the extension 250. Thus, prior to inserting the proximal attachment tube 290, the angioplasty balloon catheter, or other coronary treatment device, is withdrawn and the proximal attachment tube 290 is inserted for drug treatment or aspiration.

Thrombolytic drugs are introduced through the tube 292 of the drug delivery attachment by a syringe 306 which attaches to the luer fitting 296 at the proximal end of tube 292. Since the tube 292 has a smaller inner diameter than the guide catheter, a smaller quantity of drug is necessary to provide an effective dosage for treatment. Since a smaller dosage is required, treatment is less costly. Once in place as an extension of the guide catheter, the extension 250 can also serve to direct radiopaque solution to a selected artery.

Alternatively, if aspiration treatment is undertaken the syringe 306 is manipulated to apply a net negative pressure across the extension 250 and the tube 292 to withdraw thrombus from an occluded vessel. Preferably, a 50 cc (cubic centimeters) syringe is used.

After the drug or aspiration treatment is complete, if necessary, an angioplasty device may be reinserted for continued treatment through the proximal attachment tube 290 and the extension 250. Alternatively, the proximal attachment tube 290 may be removed and an alternate angioplasty device may be inserted through the guide catheter and the flexible tube 255 of the extension 250. In either event, extension 250 provides a guiding and "back-up" function to aid in the advancement of such devices therethrough.

Preferably, the tube 292 of the drug delivery attachment 290 has an outer diameter of 0.040 inches to 0.070 inches. The tube has an inner diameter of 0.030 inches to 0.06 inches. The length of the tube 292 is approximately 40.0 to 60.0 inches in length.

It should be noted that the figures have not been drawn to scale as it has been necessary to enlarge certain portions for clarity. Although the present invention has been described with reference to several embodiments, workers skilled in the art will recognize that changes may be made in form and detail without departing from the spirit and scope of the invention. Also, it should be understood, that the invention is not limited to the uses specifically set forth in the preferred embodiment of the invention and the scope of the invention should not be limited thereby.

What is claimed is:

1. A fluid delivery system comprising:

a relatively flexible tube having an outer diameter sized for insertion into a coronary vessel, an inner diameter defining a lumen therethrough, and a proximal and a distal end, the extent therebetween defining an extension length of the flexible tube, the length of the tube being sized so that the proximal end of the tube aligns with a distal end of a guide catheter and the distal end extends into the vessel to reach a treatment site; and a push rod attached to a proximal end of the tube for slidably positioning the tube in the vessel;

an elongated attachment tube having a proximal end and a distal end and sized for placement through a guide catheter; and coupling means for fluidly connecting the distal end of the attachment tube relative to the proximal end of the flexible tube to define a continuous lumen therealong for fluid delivery.

2. The fluid delivery system of claim 1 wherein the coupling means for fluidly sealing the attachment tube relative to the flexible tube includes a distally tapered coupling cone having a hollow cross-section, the coupling cone being sized to mate with a distally tapered proximal funnel at the proximal end of the flexible tube.

3. The fluid delivery system of claim 1 wherein the elongated attachment tube is formed of a polymer.

4. The fluid delivery system of claim 1 wherein the elongated attachment tube is 40 to 60 inches in length.

5. The fluid delivery system of claim 1 wherein the flexible tube has an outer diameter of approximately 0.056 inches.

6. The fluid delivery system of claim 1 wherein the attachment tube has an outer diameter of approximately 0.040 inches to 0.070 inches.

7. A kit for selective fluid delivery in combination with balloon dilatation, the kit comprising:

an angioplasty balloon dilatation catheter;

a guide catheter formed of a tubular member defining a guide lumen through which the angioplasty balloon catheter is guided;

an intravascular device including a flexible tube having a proximal end and a distal end and lumen therethrough, an outer diameter thereof being sized for advancement through the guide catheter and for insertion into a coronary vessel and a diameter of the lumen of the flexible tube permitting placement over an angioplasty balloon catheter;

a push rod attached to the proximal end of the flexible tube of the intravascular device for advancing the flexible tube into the vessel to align the distal end thereof at a treatment site;

an elongated attachment tube having a proximal end and a distal end and sized to extend to and align with the proximal end of the flexible tube of the intravascular device, the attachment tube defining a lumen for drug delivery; and coupling means for fluidly connecting the distal end of the attachment tube with the proximal end of the flexible tube of the intravascular device to define a continuous lumen therealong for fluid delivery.

8. An aspiration device for withdrawing clotting material from a coronary vessel, the aspiration device comprising:

a flexible tube designed for insertion into a coronary vessel to reach a treatment site, the flexible tube having a proximal and a distal end defining an extension length of the flexible tube therebetween, the length of the tube being sized so that the proximal end of the tube aligns with a distal end of the guide catheter and the distal end extends into the vessel to reach a treatment site;

a push rod attached to the proximal end of the tube for placement of the tube into the coronary vessel; and an elongated attachment tube designed for placement to the guide catheter, the elongated attachment tube having a proximal end and a distal end and sized to extend to and align with the proximal end of the flexible tube, the attachment tube defining a lumen for aspiration;

coupling means for fluidly connecting the distal end of the attachment tube relative to the proximal end of the flexible tube to define a continuous lumen therealong for aspiration.

9. A kit for selective aspiration treatment to remove blood clotting material in combination with balloon dilatation, the kit comprising:

an angioplasty balloon dilatation catheter;

a guide catheter formed of a flexible tube defining a guide lumen through which the angioplasty balloon catheter is guided;

an intravascular device including a flexible tube having a proximal end and a distal end and lumen therethrough, an outer diameter of the flexible tube being sized for advancement through the guide catheter and for insertion into a coronary vessel;

a push rod attached to the proximal end of the flexible tube for advancing the flexible tube into a vessel to align a distal end thereof at a treatment site;

an elongated attachment tube sized to extend to and align with the proximal end of the flexible tube of the intravascular device, the attachment tube defining a lumen for aspiration.

* * * * *